United States Patent
McNeal et al.

(10) Patent No.: US 7,671,733 B2
(45) Date of Patent: Mar. 2, 2010

(54) METHOD AND SYSTEM FOR MEDICAL ALARM MONITORING, REPORTING AND NORMALIZATION

(75) Inventors: Michael McNeal, Boca Raton, FL (US); Axel Souders, Palm Beach Gardens, FL (US); Mark Brezina, Kitchener (CA); Adrian Crooks, Lake Worth, FL (US); Juan Sierra, Plantation, FL (US); David Weiss, Coral Springs, FL (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 352 days.

(21) Appl. No.: 11/709,002

(22) Filed: Feb. 21, 2007

(65) Prior Publication Data

US 2007/0229249 A1 Oct. 4, 2007

Related U.S. Application Data

(60) Provisional application No. 60/783,581, filed on Mar. 17, 2006.

(51) Int. Cl.
*G08B 1/08* (2006.01)

(52) U.S. Cl. ............... 340/539.12; 340/573.1; 340/555; 340/10.5

(58) Field of Classification Search ............ 340/539.12, 340/573.1, 573.4, 517, 524–525, 501, 506, 340/521–522, 541, 552, 555, 556, 565, 567, 340/10.1, 10.5, 10.51, 10.52
See application file for complete search history.

(56) References Cited

U.S. PATENT DOCUMENTS

| | | | | | |
|---|---|---|---|---|---|
| 5,319,363 | A | * | 6/1994 | Welch et al. | 340/825.36 |
| 5,884,184 | A | * | 3/1999 | Sheffer | 455/521 |
| 5,936,547 | A | | 8/1999 | Lund | |
| 6,102,874 | A | * | 8/2000 | Stone et al. | 600/595 |
| 6,362,747 | B1 | * | 3/2002 | Parker | 340/691.6 |
| 6,366,211 | B1 | * | 4/2002 | Parker | 340/693.2 |
| 6,998,959 | B2 | | 2/2006 | Lund | |
| 7,046,120 | B2 | * | 5/2006 | Lund | 340/7.48 |
| 2005/0146430 | A1 | * | 7/2005 | Patrick et al. | 340/531 |
| 2005/0242928 | A1 | * | 11/2005 | Kirkeby | 340/286.07 |
| 2007/0192133 | A1 | * | 8/2007 | Morgan | 705/2 |

* cited by examiner

*Primary Examiner*—Daniel Previl (57) ABSTRACT

A system for monitoring and reporting medical alarms includes an alarm messenger for receiving an alarm signal from monitored equipment. The alarm signal includes information to enable determination of the location of the monitored equipment. The alarm messenger outputs an alarm messenger signal including the information. A database includes a master association table stored in the database. A central server receives the alarm signal, utilizes the information from the alarm signal to access the master association table to determine alarm information and, in response to the alarm information, notifies the appropriate staff of an alarm condition.

21 Claims, 10 Drawing Sheets

| 18 Equipment | 12 Patient | 14 Bed | 16 Room | Staff Nurse /Attendant | 210 Rules | 220 Device | 240 Record |
|---|---|---|---|---|---|---|---|
| Heart Monitor EID # 18a | Bob Jones, PID # 12a | BID # 14A | RID #402A | Jones, Betty SIN # A1 | Escalate If not accepted within 15 seconds | Paper 50 | Alarm X from EID 18a occurred at Oct 20, 2006 hh:mm:dd,accepted by NA1 at hh:mm |
| Ventilator EID # 18b | Carlos Garcia PID # 13b | BID # 14B | RID #402B | Smith, Bob SIN # B1 | Respond with medication | Nurse Station 60 | Alarm Y from EID 18b occurred at Oct 20, 2006 hh:mm:dd,rejected by NB1 at hh:, escalated mm:... |
| Infusion Pump EID # 18c | Robert Flippo PID # 12c | BID # 14C | RID #402C | Jones, Betty SIN # A1 | Specialist Required | Phone Extension 70 | |
| Nurse Call EID #18n | James Smith PID # 12n | BID # 14N | RID #402N | Campbell, Joan SIN # N1 | Basic | Pager50, Phone 70, Station 60 | |

METHOD AND SYSTEM FOR MEDICAL ALARM MONITORING, REPORTING AND NORMALIZATION

CROSS-REFERENCE TO RELATED APPLICATIONS

This application is a Non-Provisional of Provisional (35 USC 119(e)) Application No. 60/783,581 filed on Mar. 17, 2006.

BACKGROUND OF THE INVENTION

This invention is directed to the monitoring of medical alarm situations and the reporting and responding to thereof, and in particular, the managing of alarms from a disparate variety of locations, equipment, and patients associated therewith.

With the advent of modern medicine, condition monitors for patients have grown in complexity, not only in the conditions monitored, but also in the manner in which alarm conditions are reported. An industry has grown up around the monitoring technology so that a variety of manufacturers has developed their own proprietary alarm and monitoring equipment. This equipment monitors conditions and reports on conditions in a different manner from type to type and manufacturer to manufacturer. Accordingly, a Phillips monitor may monitor a patient in one way, while a Siemens monitor may monitor the exact same condition in another way. Furthermore, monitors, although quite sophisticated, merely monitor a condition and are not cognizant, nor do they care about their physical location within a hospital or the identity of the patient to which they are attached. Lastly, the monitors, because they report in disparate ways, are not conducive to providing consistent, accurate messages in a single format. Furthermore, the alarms are usually localized, i.e., occurring adjacent the patient being monitored, such as in the room, or at best, and not in every situation, at a nurse's call station.

As a result, multiple disparate alarms are triggered. The alarms occur at a variety of places and therefore are hard to monitor, audit, track or even respond to in a consistent manner. The time and effort required to monitor these disparate alarms takes away from time and effort which caregivers could be dedicating to patients. Lastly, the processing or responding to the alarms is done on a localized basis with solutions that are only available from the manufacturer of the alarm. One manufacturer designs a device that requires response by physically pushing a button on the device, while another device may allow for remote access or response from the nurse's call station.

Accordingly, it is desired to provide a system and apparatus, which overcomes the shortcoming of the prior art by centralizing the alarm collection, logging, staff assignment and response for the disparate alarm equipment.

Furthermore, when alarm reports are given, they either have too little data so that responses cannot be efficiently determined and performed, such as a red light or a sound, or too much data, such as a simultaneous wave form at a screen at a nurse's station. The first response, although quick, limits the possibilities to respond. The second type of alarm, richer in data, requires more time to generate and therefore is inefficient and may arrive too late for an appropriate response. Accordingly, there is no happy medium.

Furthermore, a caregiver at a single station may be overwhelmed by the number, complexity and differences amongst the different signals received from monitoring equipment, nurse call buttons, and other equipment signals. The information overload may result in confusion and inadequate response to true emergencies.

Even when the locations of patients and equipment are fixed relative to rooms or designated areas within a facility, the assignment of staff, in general, and which staff member in particular responds to a monitored alarm, is often a variable. It is a function of physical proximity to the alarm, schedules as determined by either the manager of the facility or the vendor of the staff (such as nurse supply companies) and the changing schedules of staff members as a function of general availability.

Accordingly, it is desired to provide a system which overcomes the shortcomings of the prior art by tracking staff, scheduling staff and assigning staff to respond to a monitored alarm in an efficient manner.

BRIEF SUMMARY OF THE INVENTION

A system for monitoring and reporting medical alarms includes an alarm messenger for receiving an alarm signal from monitored equipment. The alarm signal includes information to enable determination of the location of the monitored equipment. The alarm messenger outputs an alarm messenger signal including the information. A database includes a master association table stored in the database. A central server receives the alarm messenger signal, utilizes the information from the alarm messenger signal to access the master association table to determine alarm information and, in response to the alarm information, notifies the appropriate staff of an alarm condition.

In a preferred embodiment, the master association table maps patient identification information, bed identification information, room identification information and staff identification information. The master association table also includes rules governing the method in which the staff is notified regarding an alarm as a function of the other information stored in the table. In the preferred embodiment, the alarm messenger signal includes a text tag and image tag, so that the alarm messenger signal is first transmitted to the server and has an empty attribute for the image tag. The alarm messenger sends the text portion of the message with an expected image instruction to the central server which then transmits an alarm signal in response to that message.

In another embodiment of the invention, the personnel and the equipment assignments are stored in an assignment table within the database. An assignment templates table is stored within the database, with each assignment template containing identification information for each of the assignments stored in the assignment table so that the server is capable of modifying the assignments by amending the assignments table by utilizing the assignments templates table as an index to access the desired assignments table. The templates and assignments table may be accessed by third parties utilizing a standard software toolkit.

In another embodiment of the invention, each piece of equipment and each staff member is provided with a location based application compatible tag. The database stores one or more zones corresponding to geographical locations with a monitored facility. The server determines the geographical location of each of the tagged pieces of equipment for staff and in response to an alarm determines the closest staff member to the alarm zone or the individual equipment and sends the alarm signal to that staff member.

BRIEF DESCRIPTION OF THE DRAWINGS

For a fuller understanding of the invention, reference is had to the following description taken in connection with the accompanying drawings in which.

DETAILED DESCRIPTION OF THE INVENTION

Figure 1:
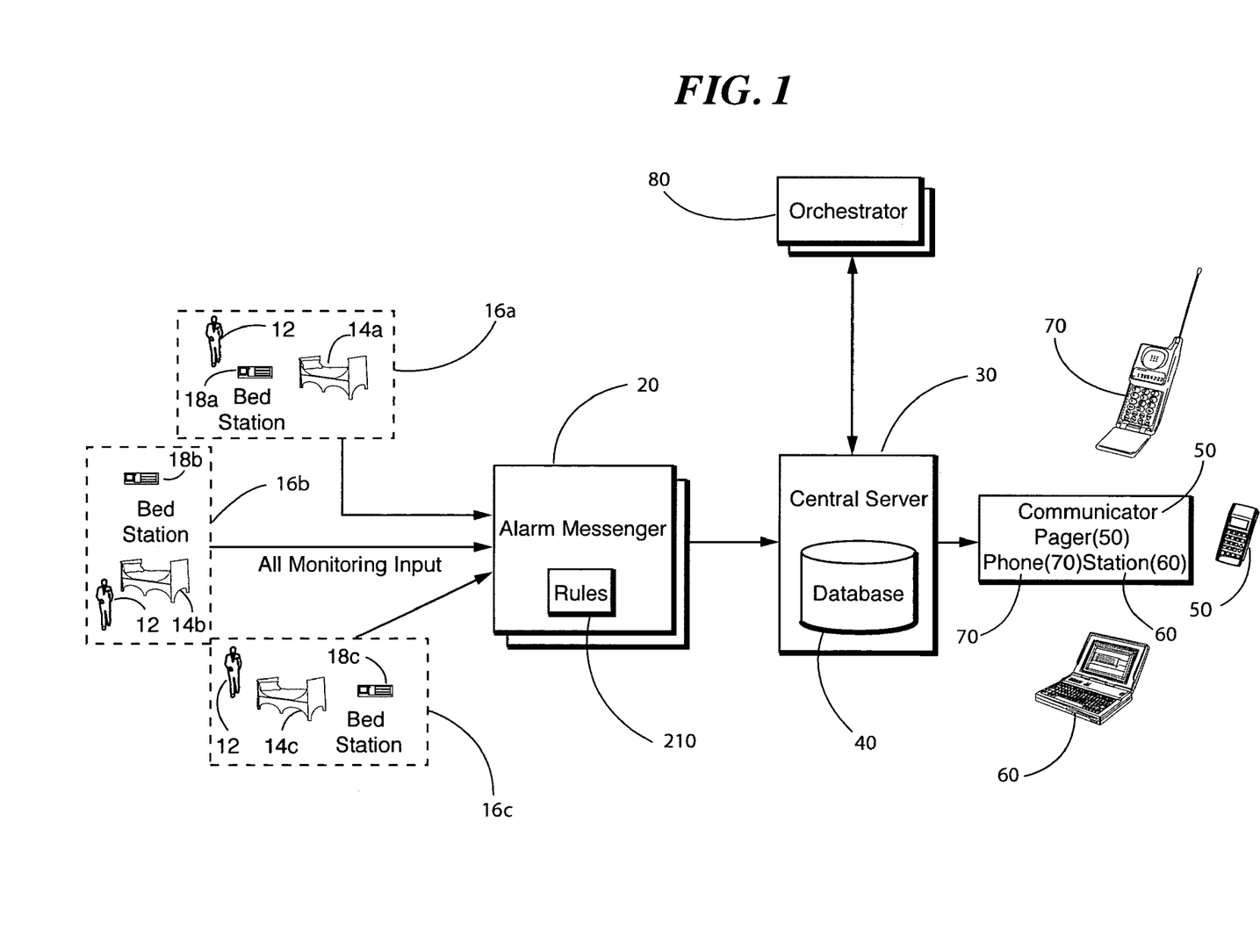
FIG. 1 is a block diagram of an alarm management system constructed in accordance with the invention.

Reference is made to FIG. 1, which is a block diagram in which a system for monitoring patient medical alerts, generally indicated as 10, in accordance with the invention is provided. One of the key issues with respect to monitoring and reporting on patient conditions is the addressability of the patient, the bed, the room, and the equipment; compounded by the fact that the equipment, patient and bed are often mobile. Therefore, as known in the art, each patient $12_a$-$12_n$ is assigned a personalized identifier. In most cases, and for ease of description, in a hospital situation where most monitoring occurs, each patient is associated with a bed $14_a$-$14_n$.

It should be understood that the invention is not limited to addressing beds, as will be clearly understood from the description below, and is applicable to patients who are being monitored ahead of being assigned to a bed, have not been assigned to a bed, or may be in a wheelchair, or the like.

Each bed is disposed within a room $16_a$-$16_n$. Lastly, equipment $18_a$-$18_n$ for monitoring, signaling, or treating patients 12 are placed in the vicinity of each patient 12. Equipment $18_a$-$18_n$ may be of different types, performing different functions and reporting conditions in different manners. However, each piece of equipment 18 is assigned an equipment identification number. By way of example, equipment $18_a$ may be a heartbeat monitor from a first manufacturer, which outputs a first signal when the heart rate exceeds or falls below a predetermined range. Equipment $18_b$ may be a ventilator manufactured by a second manufacturer, which outputs a different type of signal to a workstation. Lastly, equipment $18_n$ may be a nurse call button, or just as easily, a heart monitor manufactured by a different manufacturer than equipment $18_a$.

Each bed is assigned a bed identification number BID#. Each room is assigned a room number RID#.

Generally, each equipment 18 is in communication with an alarm messenger 20. Alarm messenger 20 receives each of the alarms from equipment $18_a$-$18_n$, processes them, as described in detail below, and transmits an alarm messenger signal to a central server 30. Central server 30 is associated with a database 40. Database 40 includes a master association table 200, which normalizes (converts them to signals of consistent format and nomenclature) the information and signals processed by alarm messenger 20.

Figure 2:
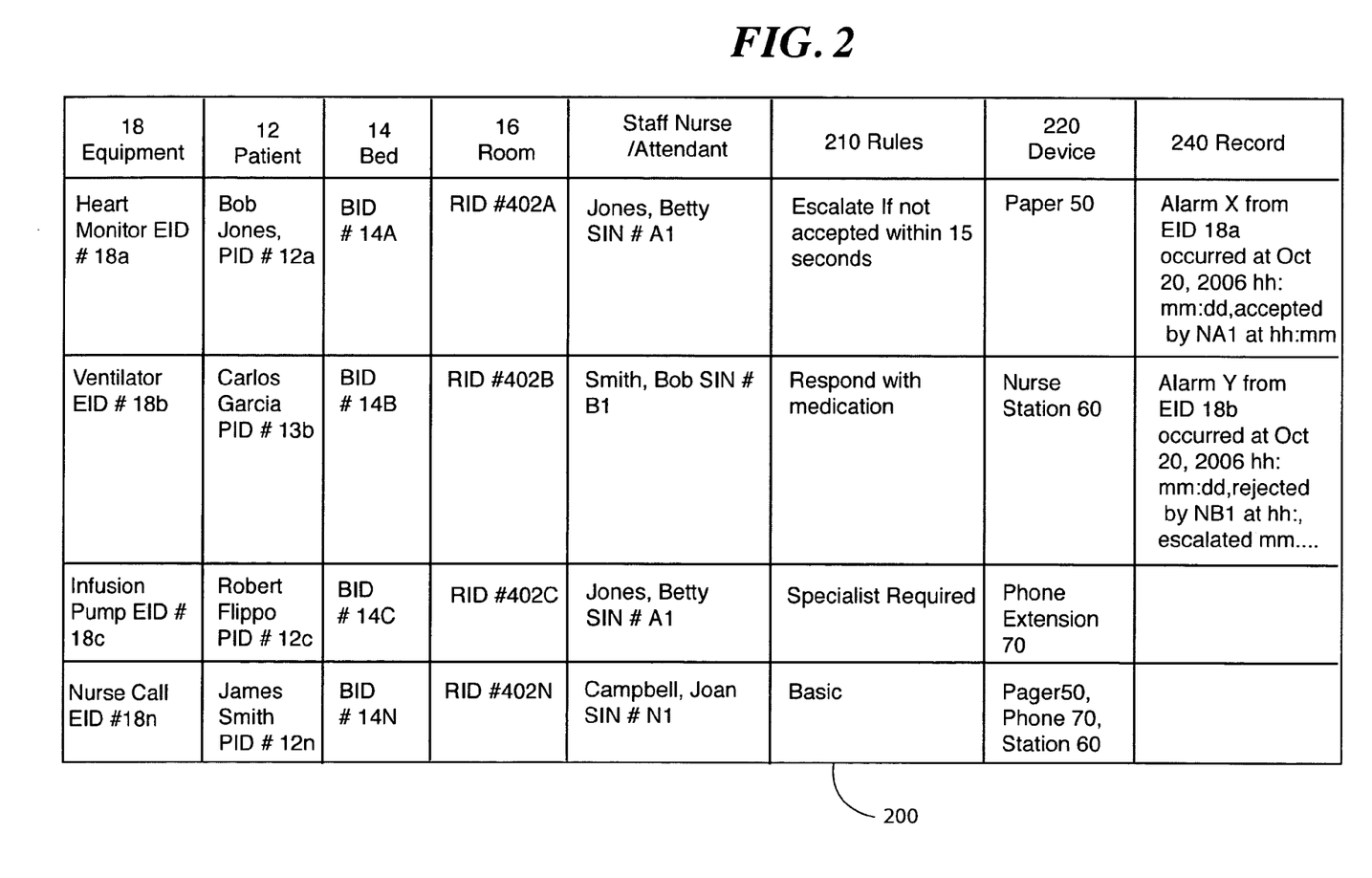
FIG. 2 is a master association table constructed in accordance with the invention.

Reference is now made to FIG. 2 in which the master association table stored in database 40 is shown. Master association table 200 associates the data to be monitored in a way that allows for efficient response to an alarm condition sensed or triggered at the equipment $18_a$-$18_n$. Accordingly, table 200 includes an equipment file in which equipment identification numbers (EID#) are stored so that equipment $18_a$ would have its own EID#, ventilator $18_b$ would have its EID# and fusion pump $18_c$ would have its own EID# on through nurse call $18_n$ which would have its own EID#.

Similarly, each patient 12 has patient identification information such as name and residence stored along with a patient identification number (PID#). The most simplified example of the PID# could be the social security number of each patient. However, to further protect the privacy of a patient, an admissions-generated number may be utilized and stored in database 40. For example, patient $12_a$ Bob Jones would be given a first PID# through patient $12_n$ James Smith of Fort Lauderdale, Fla. who would have his own PID#. Other patient identification information such as address, next of kin, and insurance information may also be stored as part of the PID# file.

Similarly, each bed 14 is assigned a bed identification number (BID#) from beds $14_a$-$14_n$. As patients check in, they are assigned beds and the PID# is mapped to the associated BID# so that in this simplified example, PID# $12_a$ would be mapped to BID# $14_a$.

Each room is also assigned its own room identification number (RID#) such as 402A, 213B, 122C through 623N. It should be noted that, in most facilities, each room is already provided a number. So to facilitate response by staff as well as the mapping function which occurs at admission, it is preferred that the actual room numbers within the facility be utilized. Each PID# and BID# are associated with an RID#, as the bed and patient are assigned to a particular room.

Lastly, staff such as nurses, orderlies, technicians, and equipment mechanics are each assigned an identification number (generically referred to as staff identification number (SID#)). As equipment 18 is brought on line and as staff is assigned to certain physical locations within a facility and/or patients, the SID# is mapped to patients 12, beds 14, rooms 16 and equipment 18 for whom they are responsible during their working hours. It is readily understood that one technician may be responsible for the repair and maintenance of several pieces of equipment and one orderly or nurse will be responsible for one or more rooms, beds, and patients.

Rules 210, associated with each situation, are stored in master association table 200 and associated with the appropriate equipment, patient and staff. In most situations, but not all, rules 210 are bed 14 and room 16 neutral. Rules, by way of example, include which staff (SID#) to notify in response to a specific report from equipment 18. By way of example, the rule may be that the staff SID# to be located for a specific alarm is a specific staff associated with a specific staff SID#, as opposed to the nearest staff member (personal nurse versus nurse currently stationed at nurse call station) or a technician; all determined as a function of the nature of the alarm.

The rules may also include the manner of response to an alarm such as the paging of a staff member, the telephoning of a specific staff member, a general alarm to the nurse call station or other monitoring station. The manner of response may be a function of equipment 18 being monitored, the identity of the staff to be notified and the type of equipment even available to that staff member.

Lastly, a further rule 20 may be escalation protocols. The failure of infusion pump $18_c$ may not require the same type of response as the failure of the ventilator $18_b$ or a flat line on heart monitor $18_a$. Accordingly, there are escalation protocols in which if a proper response has not been received at equipment 18 or some other appropriate place within a predetermined time period, the rules for which staff member to notify, and how, may change. For example, if an alarm is triggered at ventilator EID# $18_b$, an initial signal may be sent to the nearest staff member by a signal at a nurse call station or a central call station. If no response is received within sixty seconds, then a second alarm may be sent by pager to a specific staff member. If thirty seconds later no response is received, then a phone call may go out to each of the first two staff members as well as a third staff member to ensure a proper response.

A communication file 220 identifies communication method and address such as pager 50, phone 70 associated phone numbers, or nurse call station 60 with the associated IP address or signaling local area address. It should be noted that only one pager 50, nurse station 60 and phone 70 is shown. However, each individual staff member may have a dedicated pager and/or phone with a respective number.

Lastly, a record file 240 is maintained. As will be readily determined in the discussion below, central server 30 processes each alarm condition. Central server 30 utilizing database 40 makes use of the EID#, PID# and the response. Central server 30 has an internal clock and therefore may date stamp each alarm and response and store the alarm history for patients 12, room 16, staff, and equipment 18 to provide a date-stamped history of alarm conditions. This becomes a de facto audit trail and enables root cause analysis.

An orchestrator 80 acts as the interface with server 30 allowing for the input of data for the master association table 200 and the display of activity performed by central server 30 such as call logs and the like. As each alarm is processed by central server 30, it is transmitted to orchestrator 80 for display. In this way, all alarms are reported at a central location to facilitate management of the overall medical alarm response system. As each alarm is transmitted to orchestrator 80, in a preferred embodiment as discussed in greater detail below, an operator of orchestrator 80 may determine how central server 30 is to process individual alarms.

In accordance with the invention, as will be discussed below, patients are assigned to rooms 16 and equipment 18. However, it is necessary to assign equipment 18 to geographical locations within the medical facility such as rooms 16, floors, wings, departments or the like and staff 18 to either geographical locations within the hospital or to specific pieces of equipment and/or specific patients 12 or groups of patients 12. Therefore, in accordance with the invention, staff to bed assignments are created, processed and stored.

Figure 8:
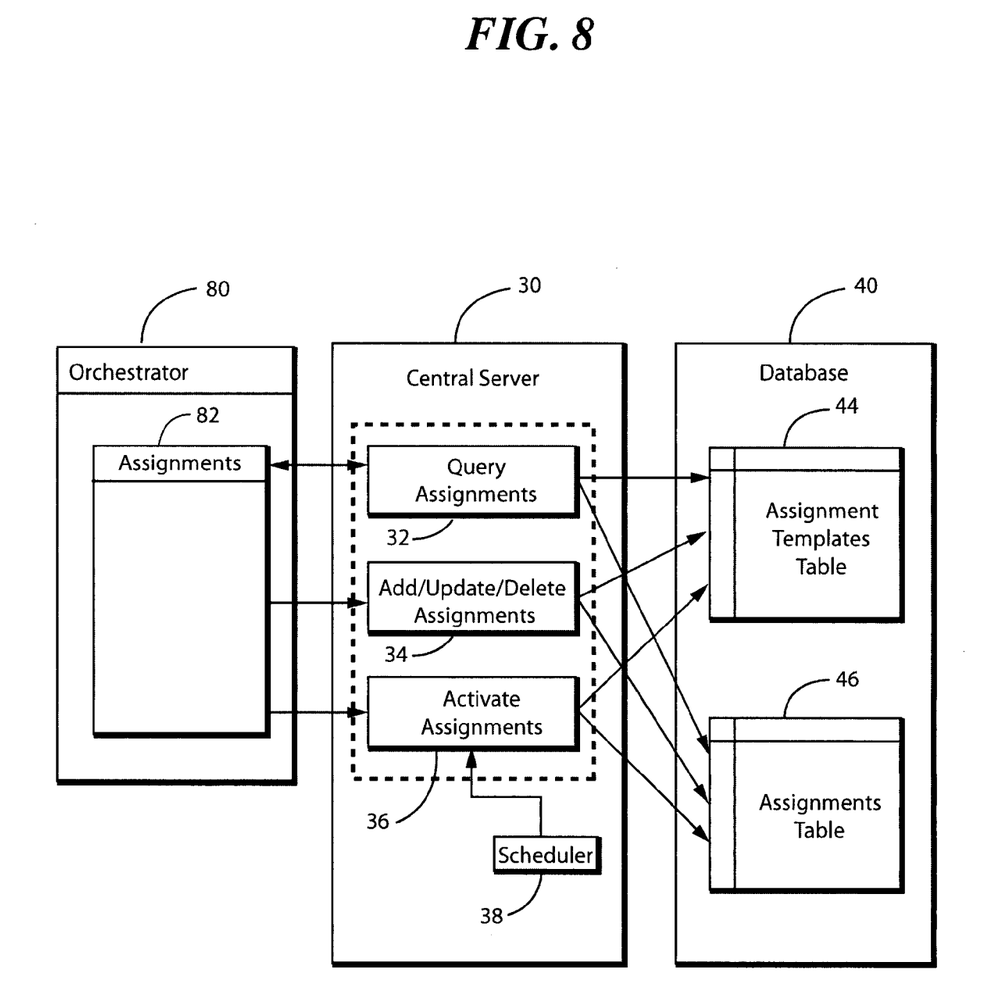
FIG. 8 is a schematic operational diagram illustrating the creation of assignment schedules for staff and equipment in accordance with the invention.

Reference is now made specifically to FIG. 8 in which an operational diagram of the process for staff and equipment assignment is provided. For ease of explanation, staff shall generically refer to one or more staff members or staff groups contained within database 40 as assignment of each of these types of entities is performed substantially the same way.

Figure 9:
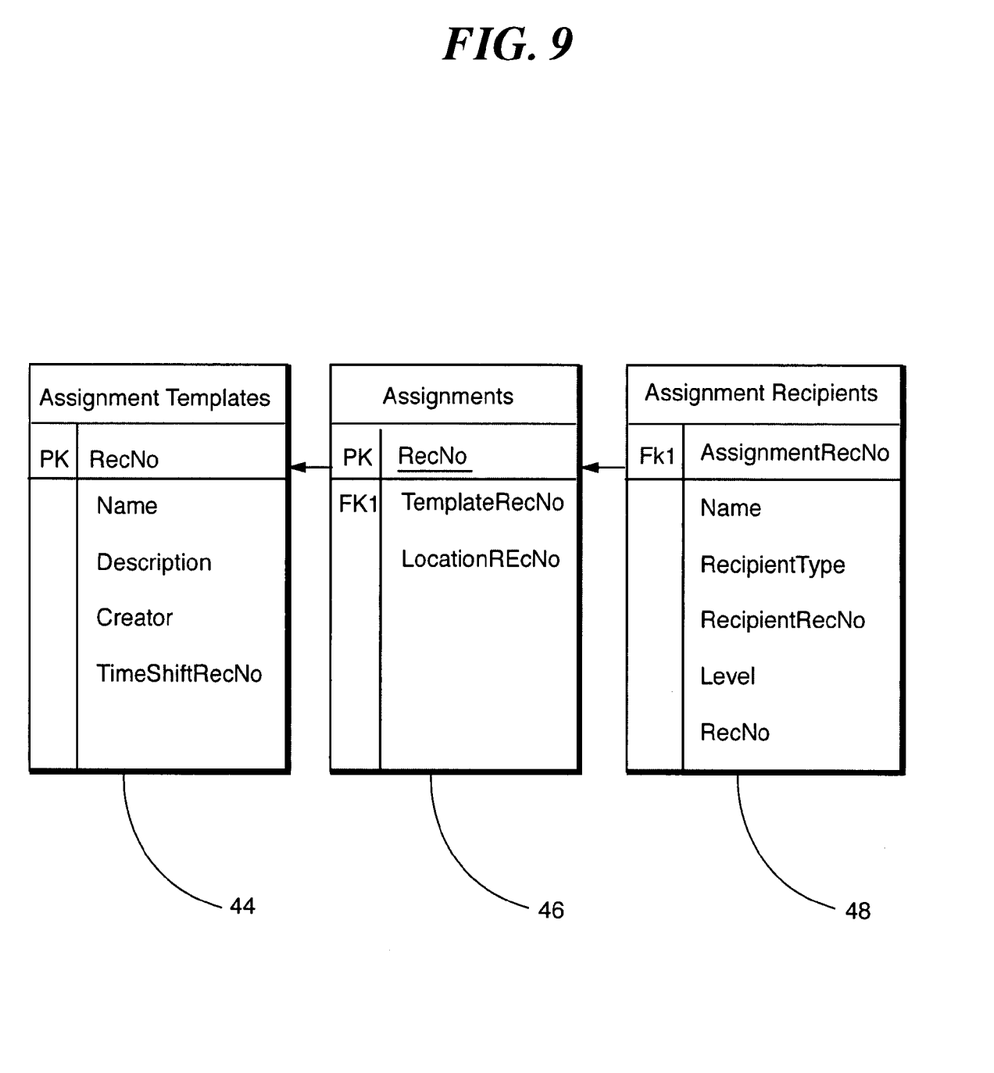
FIG. 9 is a schematic view of the database organization in accordance with the invention.

Staff assignment information is stored in database 40 by storing an assignment template 42. Assignment templates are stored in an assignment templates table 44. An assignments table 46 is mapped to the assignment templates table 44 for each assignment contained in a template. Assignment templates are in fact an index to stored assignments. Assignment template 42 will includes a record number, and the name, the description and the creator of the assignment. The template name may correspond to different shifts within the hospital schedule, individuals, or any other grouping of personnel or equipment. For each location within the hospital, the assignment table 46 stores the elements such as actual staff and their SID #, and other staff information of each set of the assignments identified in the assignment template 42.

In one exemplary embodiment for setting up an assignment, a user utilizes orchestrator 80. A geographical user interface ("GUI") is utilized within an assignments icon or assignments window 82. If initializing an assignment schedule, server 30 would be utilized to perform a function 34 to add assignments through the server interface. This function would require creating an assignment file which would begin with determining information about the assigned recipients which is a table that stores the staff information for each assignment. Assigned recipients table 48 would include assignment record number and the name, recipient type (nurse, orderly, doctor, type of equipment, or the like) to identify the specific staff member being assigned, the recipient record number, the response or authorization level, and a record number. In short, it is a record of who is assigned to each bed 14 and at what level within the response chain.

This information is then stored in assignments table 46 and includes the template record number and the location record number of the information stored in the assigned recipient's field. The identification information for identifying the assignment table is then stored as discussed above in the assignment template 44. If an assignment is active, i.e., the assigned staff are currently working as assigned, there is a template record number equal to 0 in the assignment table and no corresponding record in the assignment template table as it is currently being implemented.

Saved assignments can be edited using the assignments window 82 without having to make any particular staff assignment active. The scheduling can go on in the background.

In order to change any stored schedule, the user through window 82 at orchestrator 80 could perform a query function 32 at central server 30 to communicate with assignment template table 44 and assignment table 46 to determine the current status and makeup of any assignment record. Changes can then be made at orchestrator 80 utilizing the add/update/delete assignment functionality 34 to amend the assigned recipients field 48 and store the appropriate locators at assignment table 46 and assignment template table 44.

Staff assignment processing may include making changes as discussed above, applying an assignment set, or using current assignments to process alerts. A saved assignment set may be activated manually through orchestrator 80 and the activate assignments function 36 of central server 30 which in response to a command will activate the desired staff.

Alternatively, a scheduler 38, making up part of control server 30, acts as a schedule clock and can cause active assignments 36 functionality to be performed at pre-scheduled times. Therefore, staff activation would happen automatically. When a saved assignment set is activated, the current staff for each bed in the saved set is dropped and replaced by a new set. By way of example, shift 1 is replaced by shift 2 and the corresponding personnel. As is readily understood, the assignment templates table, assignments table and assigned recipients make up additional fields in the master association table 200.

It should be noted that the above description was in terms of personnel for ease of description. However, the assignment system and method discussed above is equally applicable to the assignment of equipment to beds. It should also be noted that such a system lends itself to third party users, parties outside the system, such as equipment manufacturers, hospital personnel staffing companies or the like so that they may also provide input to use of their resources.

As discussed above, the master association table 200 is used to determine the location and relationship of all the elements of the system, normalize alert sensitivity and to apply the notification level rules to each staff member. Third parties utilizing software development kits, such as SOCKET development kits or SOAP development kits can utilize orchestrator 80 to set schedules. A third party vendor of personnel or equipment can define their own schedules by interfacing with orchestrator 80. Then either they or the administrator of the entire system can assign the appropriate personnel to the appropriate bed with the appropriate response sensitivities.

During operation, as each patient $12_a$-$12_n$ is admitted to a facility, they are assigned a PID# to identify them. At admission, they are assigned a bed, if applicable, and a room with the associated BID# and RID#. This information is stored and mapped in database 40. As doctors and staff assign equipment $18_a$-$18_n$ to the respective patient $12_a$, the EID# associated with the equipment $18_a$-$18_n$ associated with patient $12_a$ is stored in database 40. At the same time, staff is assigned to respective patient $12_a$, as is known in the art, as a function of monitoring needs and patient condition needs and/or requested services the associated SIN# corresponding to staff assigned to patient $12_a$ are also stored in database 40. The various identification and rules stored in database 40 are associated, tagged or mapped to each other in master association table 200.

When an alarm triggers from equipment $18_a$, by way of non-limiting example, the alarm is sent to alarm messenger 20. Alarm messenger 20 receives the alarm, normalizes the alarm condition to an a alarm messenger signal recognized by central server 30 as a universal indicator of a condition such as flat line.

The location signal from equipment $18_a$ may be equipment or manufacturer specific, i.e., may be in a format unrelated to the expression of location as understood by the staff. To address this, Master Association Table 200 includes an Alias Transformation Section, which "translates" the disparate equipment indicators into a common universal indicator. For example, equipment $18_a$ may output SN423B to indicate the staff recognized Room 324C. Accordingly, central server 30, utilizing the universal signal, determines the patient 12 from the PID#, room 16 from the RID#, and bed 14 from the BID# as determined from master association table 200. From master association table 200, it is determined which staff member(s) are to be notified in accordance with which rules 210.

By way of example, if it is determined that Betty Jones is to be identified, in the first instance, at nurse station 60, central server 30 sends a signal to nurse Jones at station 60. However, if the rules indicate that nurse Jones is only to be contacted by pager 50, then central server 30 sends a text message to pager 50. Central server 30 date stamps the time and date of the alarm.

Nurse Jones then responds to the alarm with the appropriate response, summoning a doctor, acknowledging receipt at station 60 or pager 50 or at equipment $18_a$ itself. The response date and time and the nature of the response taken is also monitored by central server 30, either through communication with station 60 or as reported from alarm messenger 20 from equipment $18_a$. Central server 30 makes a record of the date, time, equipment number, patient number and the type of alarm and response, which is stored in database 40.

More specifically, during operation, alarm messenger 20 extracts key information from the alarms as received from the monitored equipment $18_a$-$18_n$. This key information may include the alarm location as in the associated room, the EID#, the PID#, or other account information. That information, as known, is transmitted to central server 30. Central server 30 makes use of the master association table by utilizing the key information to determine the location of the equipment 18 triggering the alarm. If location is not provided, then other key information such as the PID#, EID# or omnibus account number may be used in conjunction with the master association tables to determine the room location of the equipment. Central server 30 logs the alarm for reporting purposes and the alarm text is dispatched to either station 60, pager 50 or phone 70 to the appropriate staff member.

Figure 3:
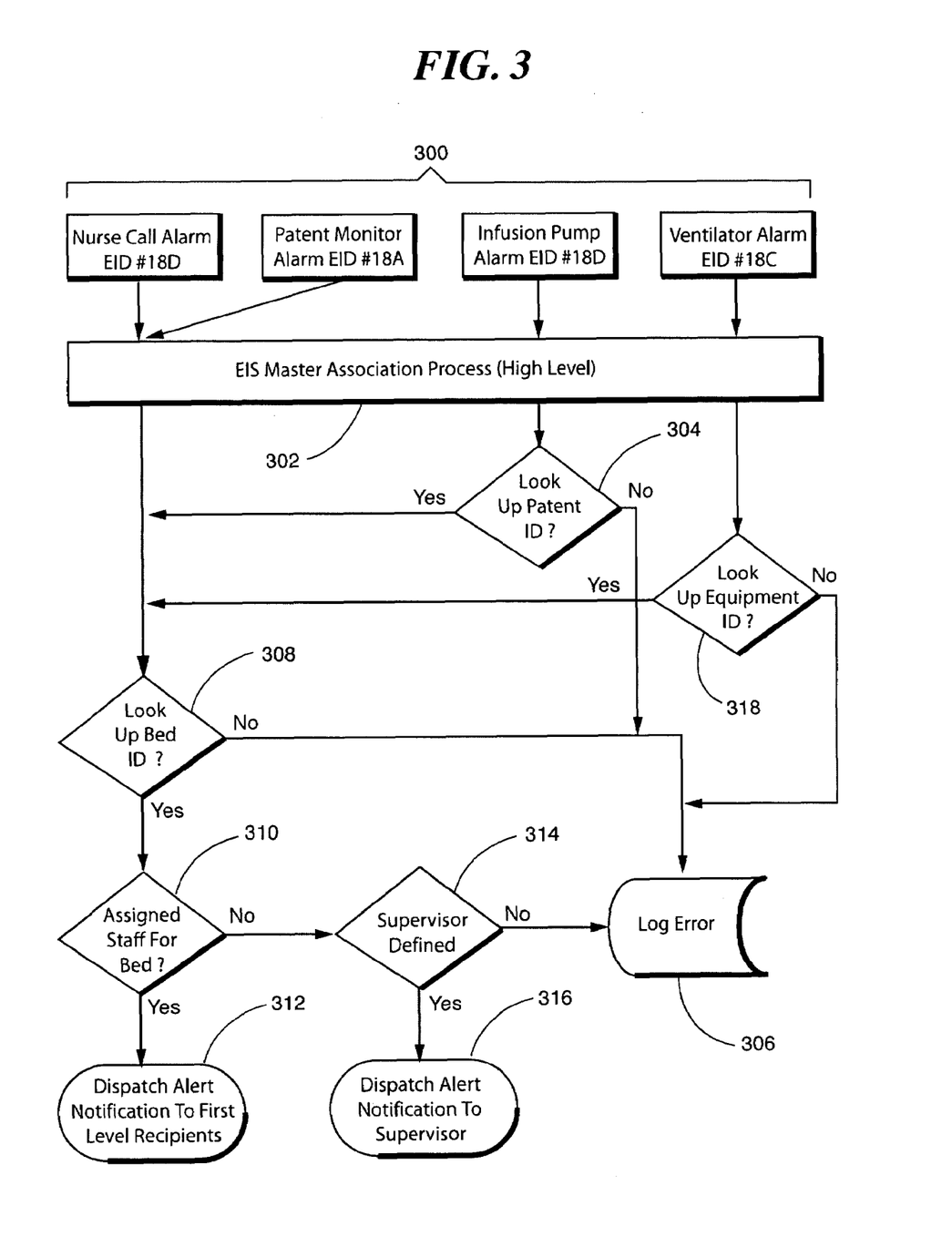
FIG. 3 is a flow chart for the operation of an alarm messenger and service in accordance with the invention.

Reference is now made to FIG. 3 in which an operational flow chart for the operation of the generic system 10 is provided.

In a first step 300, one of equipment $18_a$-$18_d$ sends an alarm-to-alarm messenger 20. In a preferred embodiment of the invention, the alarm itself includes some identification value. For a nurse call alarm, which is associated with a specific bed, it may be the bed address BID#. Similarly, the patient monitor alarm is associated with a patient or a bed and again transmits a bed label value to the alarm messenger, i.e., the BID#, PID#, or some number understood by equipment 18 which is mapped or translated by alarm messenger 20.

Equipment $18_c$ such as an infusion pump alarm may identify itself by an EID# or PID# value. This is because an infusion pump is assigned to an individual patient rather than to beds or rooms. Lastly, with equipment such as a ventilator alarm which is more likely associated with a room, the signal to alarm messenger 20 may identify the equipment by its EID# or BID#.

In a step 302, the alarm messenger 20 pares down and normalizes the central information such as the transmitted ID#. The ID# is used at central server 30 in association with master association table 200. First, it is determined whether there is a PID# in a step 304. If no, a log error is transmitted by central server 30 to appropriate staff in a step 306. In response to the log error, protocols are put in play to identify the nature and source of the alarm. If a PID# is present, it is determined from master association table 200 whether there is an associated BID# in a step 308. If there is no BID#, then a log error is produced in step 306. If there is an associated BID# or address, it is then determined from master association table 200 whether there is a staff assigned to that bed in a step 310. If yes, central server 30 dispatches an alert notification to the staff by the associated SID# in a step 312. If there is no specific staff to that identified bed, then it is determined in accordance with the rules whether or not a supervisor or secondary staff member is associated with the BID# in a step 314. If there is no defined supervisor or secondary staff member, a log error is issued in accordance with step 306. However, if there is an associated supervisor or secondary staff member, then central server 30 issues a dispatch alert notification to that associated staff member in a step 316.

The above example was the processing in connection with a device such as an infusion pump alarm having an expected associated PID# or EID# value. However, equipment 18 having an associated BID#, such as a nurse call button, would be processed directly at step 308. On the other hand, alarm signals with associated EID#s would be processed from step 302 in a step 318 in which the EID# would be looked up in master association table 200. If there was no EID# found, then a log error would be issued in step 306. If there was an EID# in step 318, then the process would return to step 308 as discussed above.

By utilization of a master association table 200, centralized alarm collection, logging and staff assignment in response to different alarm equipment indicators of disparate manufacture and operation is provided. Multiple assignment databases are reduced to a single database, the master association table 200 replaces a plurality of databases associated with each individual equipment type by function and manufacturer. Having a single processor of alarms, which normalizes the required response, and presentation of information, reduces training time and the time it takes to make assignments. Lastly, new alarm sources can be added by providing an input from the new equipment into alarm messenger 20.

Alarm messenger 20 removes portions of each signal and extracts the location of the device as reported by the device in its own unique manner, the severity of the signal and the text of any message and normalizes this alarm message by putting it into a single format. Alarm messenger 20 utilizes XML to format the message. Alarm messenger 20 also recognizes duplicative alarms and filters the duplicative alarms so that responding staff is neither overwhelmed nor confused.

As equipment 18, in particular condition monitors, become more sophisticated, the alarms may contain more and more data. For example, a heart monitor device may in fact send the recent wave signal of the heart as transmitted both ahead of and just after the alarm. Although this information is important, it is complex and requires significant bandwidth to convey. In a hospital situation, the speed of response may significantly affect the level of care given and the ability to correct the condition, which triggered the alarm. Sending a high volume of information may slow down the ability to send the alarm signal to the appropriate staff member.

Accordingly, to balance the urgency of the alarm with the need for information, the alarm messenger signal output from alarm messenger 20 to central server 30 and from central server 30 to staff devices 50, 60, 70, is formatted in multiple stages.

Figure 4:
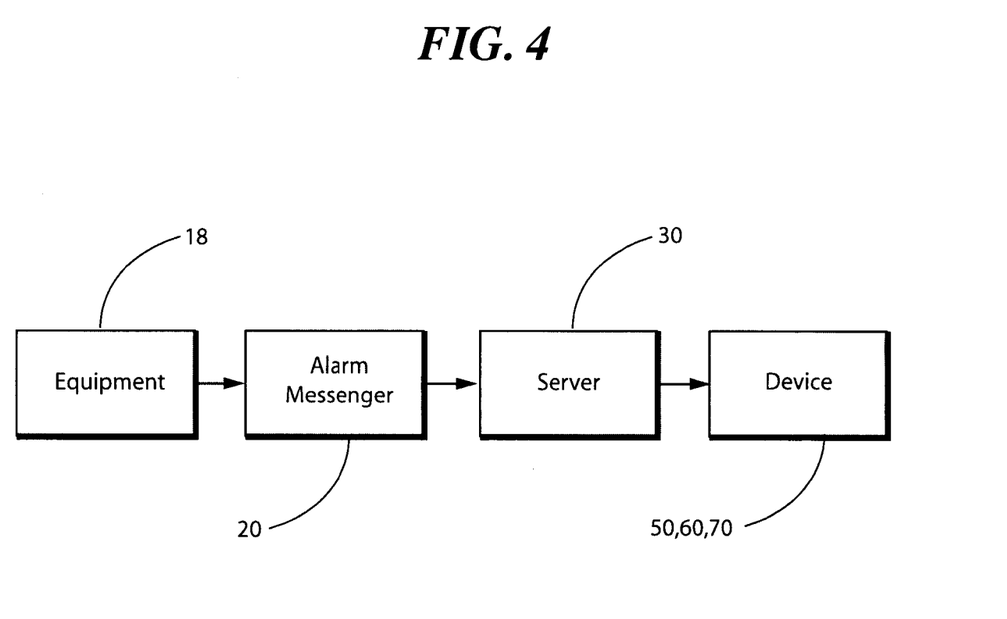
FIG. 4 is a data flow diagram for message construction in accordance with the invention.

Reference is now made to FIG. 4 where an operational flow diagram of a message signal constructed in accordance with the invention is provided. Equipment 18 outputs an alarm message. Alarm messenger 20 receives the message and formats the message by applying XML attributes to the alarm message. Alarm messenger 20 saves the machine language record number and the message ID.

The formatted XML message includes text tags and an image tag. The attribute of the image tag is originally set as empty. An expected attribute set corresponding to the number of images is associated with the alarm message. The alarm messenger 20 sends the text portion of the message with the expected image instruction to central server 30. Alarm messenger 20 immediately sends the text message and server 30 knows in turn to send the same message to the appropriate device identified in master association table 200 for responding to this message.

The server in turn informs the device 50, 60, 70 that the device should maintain an appropriate placeholder for uploading images. Alarm messenger 20 has indicated the size of the image, which is passed downstream, the device 50, 60, or 70 examines the incoming multi-part tag message, allocates the required image space, and awaits a portion of the message and the image to be downloaded to the device. However, in the interim, the appropriate staff has been notified of the nature and address of the alarm.

By utilizing XML messaging, it allows more flexible message submission as the attributes of the message and nature of the message travel with the message itself and a parser, as known in the art, is capable of acting on any attribute of the message, no matter in what order transmitted. Among the tags in the message, may be the recipient, a message or text, callback number, image, priority indicator, device escalation information, alarm sensitivity, alarm point and more, by way of non-limiting example. In this way, the message within system 10 becomes platform independent.

Figure 5:
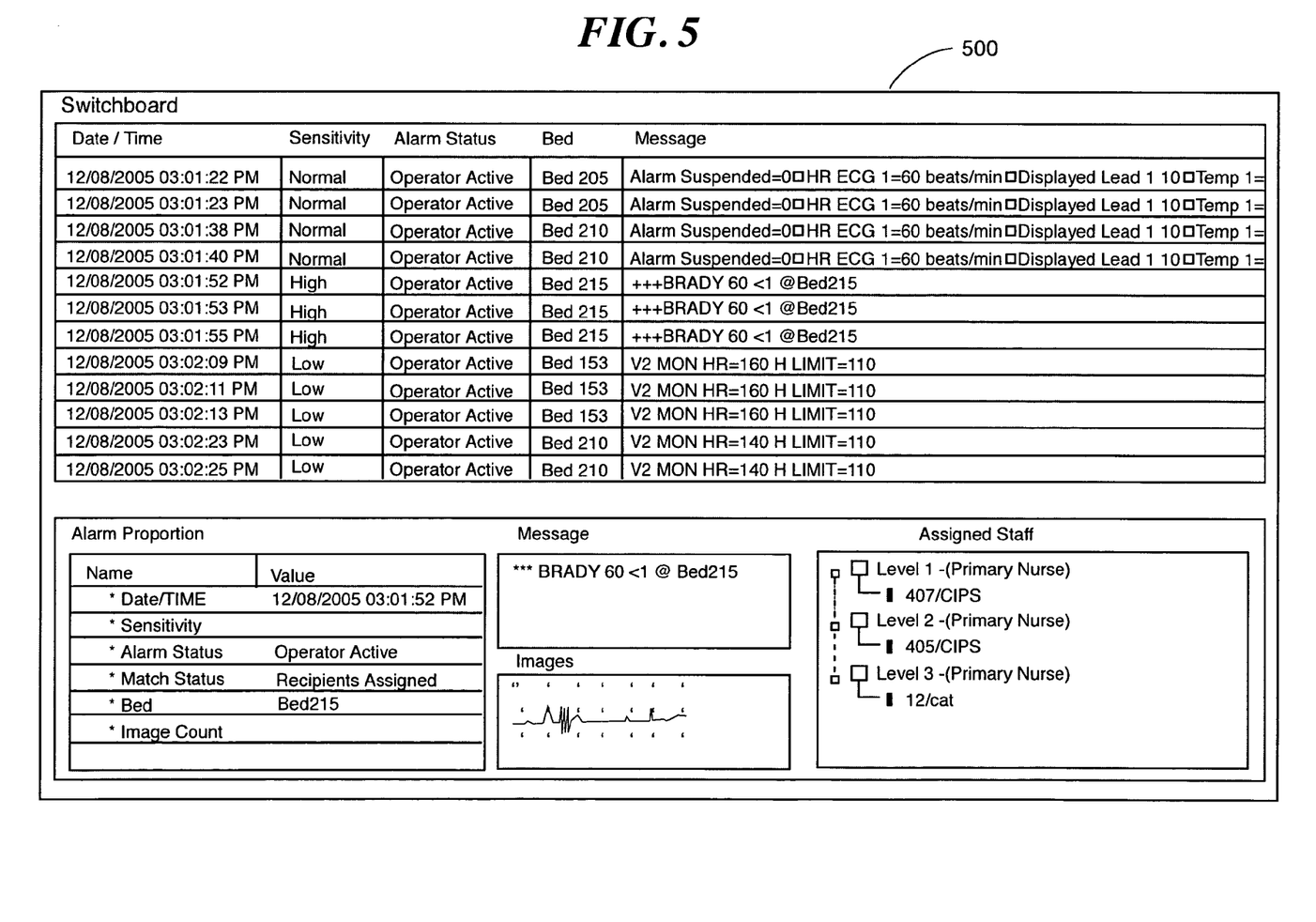
FIG. 5 is a screen shot of an alarm display in accordance with the invention.

During operation, central server 30 sends alarm information to orchestrator 80 where it is displayed for viewing at a central location. An exemplary display is shown in FIG. 5 which shows a screen shot as presented by orchestrator 80 which includes the date/time stamp of the alarm, the sensitivity of the alarm (low, normal, high), the alarm status (cancel, operator active), along with the bed location and any text or image message.

Given staffing realities, staff members can be overwhelmed with messages and inefficiently prioritize responses. Accordingly, not all messages need be sent directly to the associated or indicated staff member. In a preferred embodiment, the concepts of alarm sensitivity and priority are applied to the processing. Sensitivity refers to the nature of the alarm as it applies to staff functional areas of responsibility and capability. Central server 30, therefore, determines as a function of the sensitivity of the alarms, which alarms to send directly to the devices 50-70 and which alarms to forward to devices 50-70 only in response to an instruction from orchestrator 80. Priority refers to the relative order in which alarms require a response. The priority may be a function of the equipment that is sending the signal or alarm. Accordingly, sensitivity and priority indicators associated with each piece of equipment are stored in master association table 200 to normalize the priorities and sensitivities of the varying signals from the different equipment $18_a$-$18_n$.

In an example, a high priority message received at central server 30 will be sent directly to the appropriate staff member as determined utilizing master association table 200. Simultaneously, for monitoring purposes, the high priority alarm message will be sent to orchestrator 80. In this way, there is no slowdown of the response to high priority alarms. At the same time, an operator centrally located at orchestrator 80 can monitor whether a response has been performed.

If a low sensitivity or normal sensitivity signal is received at the orchestrator, then an operator at orchestrator 80 may determine whether to send it to the indicated communication device, i.e., page the appropriate caregiver, cancel it, if it is seen as a self-correcting measure, a response that can take care of itself, or something sent in error, or switch the staff member recipient by sending instructions to central server 30.

Figure 6:
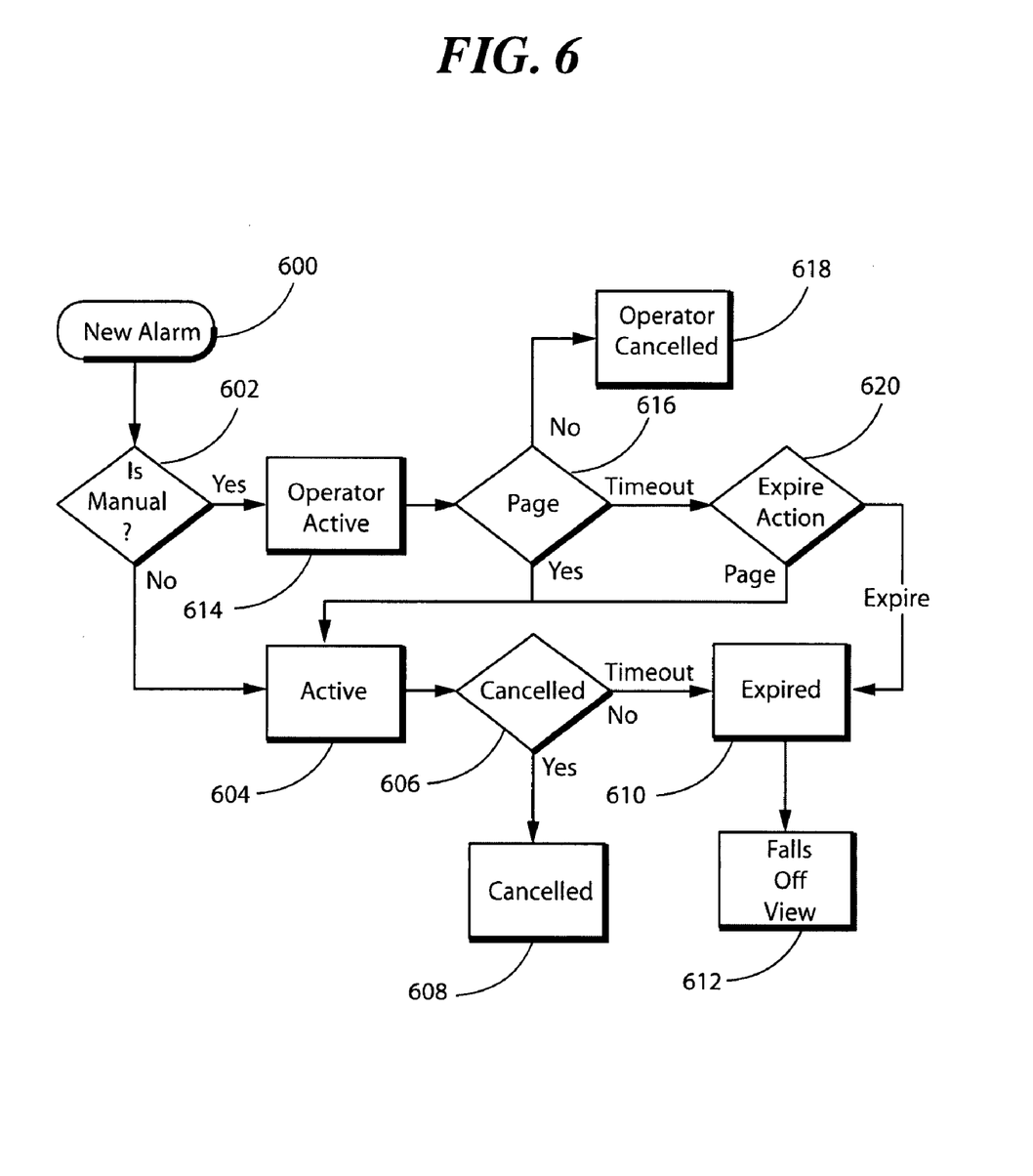
FIG. 6 is a flow chart for management of the alarms in accordance with the invention.

Reference is now made to FIG. 6 in which a flow chart for the operation at orchestrator 80 is shown. In a first step 600, a new alarm is received from central server 30. It is determined in a step 602 whether or not manual intervention is desired, i.e., is it a type of device and of sufficient sensitivity such that central server 30 has already simultaneously indicated the alarm to the appropriate staff member. If in fact no manual intervention is required, then in a step 604 the alarm is active and displayed at screen 500, but paging has already occurred. It is then determined, in a step 606 whether the alarm has been responded to or canceled. If it has been canceled in a step 608, then as will be discussed in detail below, the response is logged and no further action is required. If it has not been canceled, as determined in step 606, then it is determined whether a predetermined time interval has passed. If a predetermined time interval has passed, then the alarm is considered timed out and to have expired in a step 610.

The time interval is usually approximately fifteen minutes in an exemplary preferred embodiment. As is known in the art, during the time interval, steps 604 and 606 are iterated to allow for escalating the response in accordance with the rules 210, such that if the alarm is not canceled in a first predetermined time period such as one minute, then a page is sent out again to either the initial staff member or a secondary staff member. In a preferred embodiment, there are at least three escalating iterations of alarm notifications.

If in step 602, it is determined that the alarm is of the type in which manual intervention is desired, the alarm is considered operator-active in a step 614 so that an operator is aware and enabled to intervene. It is determined by the operator in a step 616 whether to page the alarm. If it is decided not to page the alarm, then the operator cancels the alarm in step 618. If it is decided to page the alarm, then the alarm goes active and is paged in accordance with step 604 and the escalation and timeout procedures are followed as discussed above. If, however, the operator does not cancel the operation or page the operation in a predetermined time period, it is then determined whether to expire or end any alarm in a step 620. If it is determined not to expire the action but to page the action, then the alarm goes active in accordance with step 604. If it is in fact intended to be timed out, then the alarm is expired in accordance with step 610 and falls off screen 500.

As is readily apparent, because alarm messenger 20 receives inputs from all of equipment $18_a$-$18_n$, an alarm is not just a failure or monitored danger position. Responses to alarms are either received directly from devices 50-70 at central server 30, or at the device itself when the response must be performed at equipment 18. These responses are treated as alarm message and processed as a normal or low priority signal logged and date stamped as below, and monitored at orchestrator 80.

Figure 7:
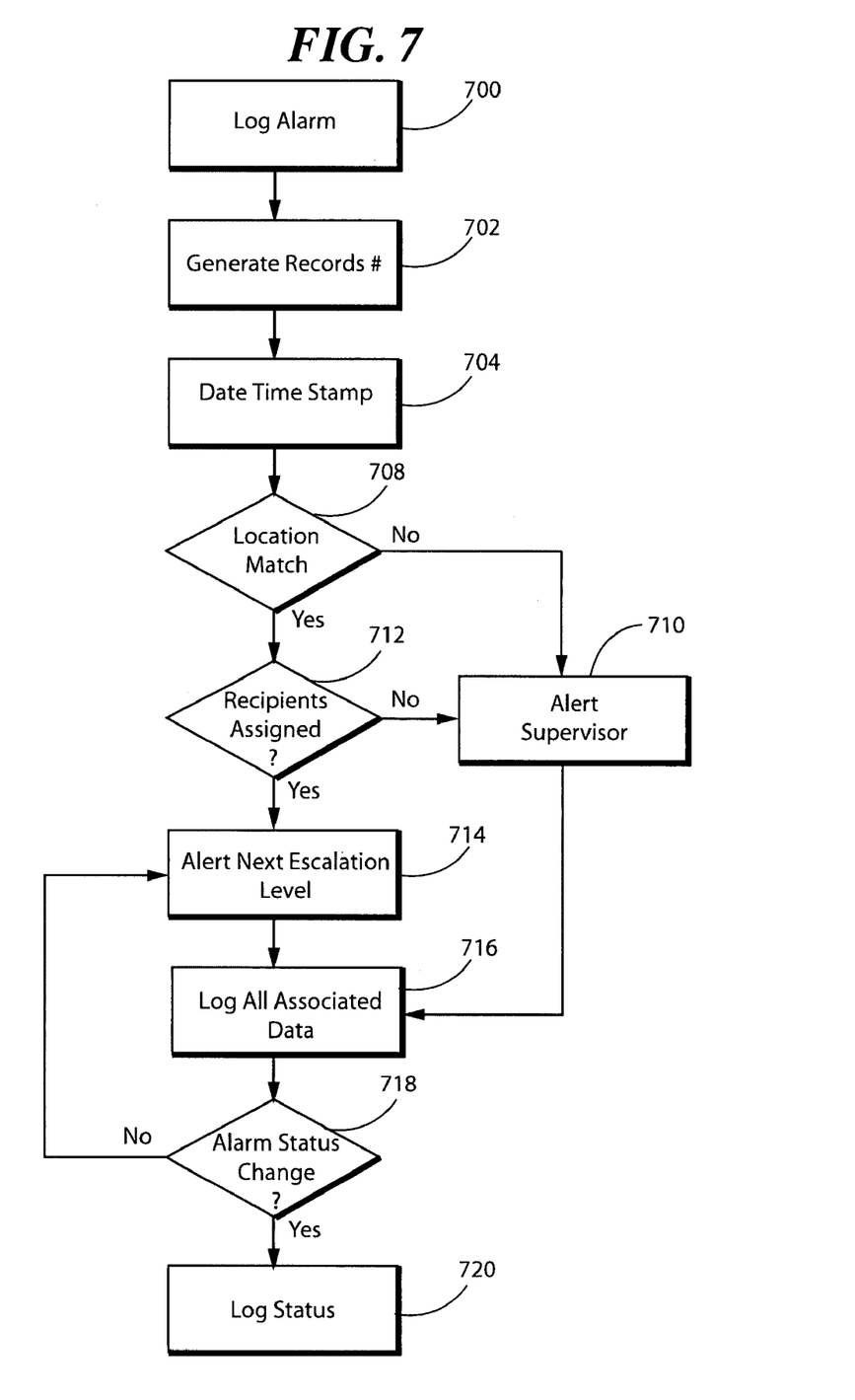
FIG. 7 is a flow chart for creating an alarm root cause analysis in accordance with the invention.

Reference is now made to FIG. 7 in which a flow chart for creating a log for each alarm is created. An alarm is logged by central server 30 in a first step 700. In a step 702, a unique record number is created and stored with the incoming alarm information in database 40. In step 704, each alarm is date and time stamped, the date and time of the receipt of the alarm being recorded in the log of database 40 with the associated record number.

In a step 708, it is determined whether the information in the alarm matches any information in the master association table 200 so that a physical location of the alarm may be determined. Based upon the information forwarded by alarm messenger 20, the location of the alarm may be determined, as discussed above, utilizing any one bit of known information and the master association table 200. If a location match is not found, in other words the location of the alarm is not in the system, then as a default a supervisor or some other staff assigned to prevent any alarm from going unanswered is notified in a step 710. In a step 712 it is determined whether a recipient has been assigned in master association table 200, if not, a supervisor is notified in step 710.

As discussed above, central server 30 and alarm messenger 20 monitor the responses to alarms. As is known in the art, if an alarm is not answered, then escalation procedures occur. For example, as discussed above, central server 30, in accordance with rules 210 may notify a secondary or tertiary associated staff member if a first assigned responder does not answer an alarm within a predetermined time period. In a step 714, the associated staff member, as determined from the SID# in master association table 200, is alerted. If no alarm has been sent, then the first responder staff will be notified. The escalated message is logged with the resolved location and at least one of EID#, alarm sensitivity, alarm type, equipment vendor and PID# in a step 716 with an associated message ID number.

It is determined in a step 718 whether the alarm status has changed (i.e., been resolved). If not, the alarm procedures are escalated in accordance with rules 20 at step 714. Steps 714-717 are repeated for each escalation. If there is a change in status (i.e., resolution), then the response is logged in a step 718.

As each response to an alarm is treated as an alarm signal, the response is logged with the associated record number. The response is date stamped, the nature of the response, the SID# for the responding staff is logged with the associated record number.

All of the logged data and their associated record numbers may be combined so that the message log status can be combined with the alarm log information to produce a root cause analysis. The message log status, as can be determined from above, consists of a time stamped log of each dispatched status. By tracing the record number thread, it is possible to audit the entire operational trail of an alarm from generation to response, including intervening escalation stages and changes in status. All of this information is stored in database 40 and may be manipulated and viewed at orchestrator 80.

As discussed above, alerts are provided to staff based upon predefined rules. However, in some circumstances, the best responder may in fact be the staff member closest to the alarm, which may not always be the preassigned responder. In some cases, determination may be made as a combination (assignment and proximity) of the two requirements in that the closest preassigned responder would respond to the alert, not necessarily the first responder in the hierarchy. Therefore, a location-based response logic is provided for the system. In an alternative embodiment, each communication device 50, 60, 70 is provided with location-based applications. Alternatively, each staff member or piece of equipment can be provided with a location based application compatible device for which a physical location may be determined. In other words, as known in the art, devices report back their physical location. Accordingly, the physical location of the staff member associated with the communication device can be determined and logged. In this way, the information can be used for staffing and positioning studies.

In this embodiment, zones of one or more rooms or other geographical location within the facility are stored. Each staff member and article of equipment carries either a badge, tag, transponder or the like which is location-based application compatible or a location-based enabled communication device. The identity of these devices and the staff and the equipment to which it is assigned is stored in the master assignment table 200.

Figure 10:
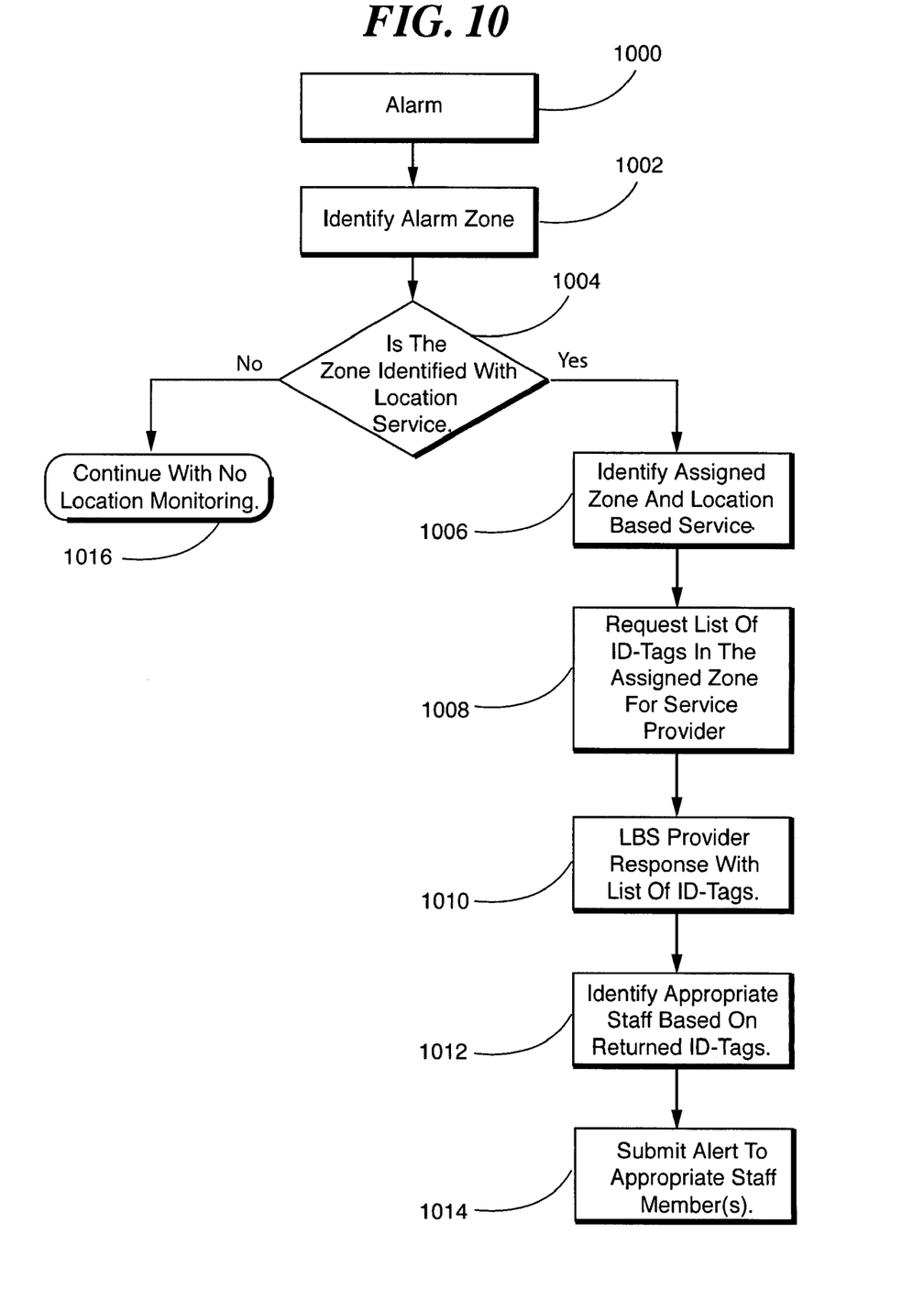
FIG. 10 is a flow chart for execution of a location-based embodiment for responding to alarms in accordance with the invention.

Reference is now made to FIG. 10 where a flow chart for a method of responding to alarms under a location-based protocol is provided. In a step 1000, an alarm is identified by server 30. In a step 1002, the alarm zone is identified from master assignment table 200. In a step 1004, it is determined whether or not the alarm zone is associated with the location-based service ("LBS"); i.e., location of that kind of equipment and personnel capable of being identified. If not, then the process continues in a step 1016 as defined above. If it is a location-based service enabled zone, then server 30 searches the master access table 200 for the identity of the assigned zone and the vendor of the location-based services. It should be noted that the location-based service vendor is identified and stored in database 40.

In the preferred embodiment, an outside third party vendor performs the function of comparing the location of the zone or specific location of the alarm within the zone and of the staff and equipment 18 to make the relative location determination. In a step 1008, server 30 requests a list of the LBS tags within the assigned zone from the service provider. In a step 1010, LBS provider forwards the list of identification tags. In a step 1012, server 30 identifies the appropriate staff based on the returned identification tags and submits the alert to the appropriate staff members within the zone as determined in step 1008.

In step 1010, a filter function is performed as a function of the sensitivity or priority of the alert. If three doctors and four nurses are identified as being within the alarm zone, depending on the nature of the alarm and the sensitivity or priority, the nurse may be alerted first and then a doctor in accordance with similar rules as those discussed above. However, if the type of alarm is skill set neutral server 30 may alert the nearest staff member or the nearest nurse if a doctor's expertise is not needed.

It should be noted that once personnel and equipment are provided with location-based application-ready equipment, the location of the equipment and personnel can be monitored. Therefore, if a rule assigns equipment or staff to a zone during a shift, if the equipment is improperly moved from the zone, or the staff breaks a rule and leaves the zone, an alarm can be sent to by server 30 to alert an administrator at orchestrator 80 to determine whether such movement is permissible or an event which needs to be remedies.

By utilizing a location-based embodiment, the response time to active alarms may be reduced by taking advantage of the most available resources and personnel rather than preassigned personnel that may not be available to respond to every alert as it occurs.

Furthermore, functionality has been divided between alarm messenger 20, server 30, and orchestrator 80. However, this is done for ease of explanation and it should be understood that the functionality may be located in one single device, two devices, or more, or bifurcated among the three in many different ways as would be known to one skilled in the art.

What is claimed as new and desired to be protected by Letters Patent of the United States is:

1. A system for monitoring and reporting medical alarms comprising:
    an alarm messenger which receives, from monitored equipment, an alarm signal including information indicative of a location of the monitored equipment and outputs an alarm messenger signal including the information, the alarm messenger signal including a text tag and an image tag, the alarm messenger signal as first transmitted from the alarm messenger having an empty attribute for the image tag, the alarm messenger sending the text portion of the alarm messenger signal with an expected image instruction,
    a central server which receives the alarm messenger signal from the alarm messenger and sends an alert in response thereto;
    a database, a master association table stored in said database, said central server receiving said alarm messenger signal, utilizing the information from said alarm messenger signal to access said master association table to determine alarm information and, in response to said alarm information, notifying appropriate staff of an alarm condition.

2. The system of claim 1, wherein said central server date stamps each alarm messenger signal received, creates a log of each alarm messenger signal stored in said database, receives alarm response information from the alarm messenger, date stamps the response information and stores the response information in the log.

3. The system of claim 1, wherein the alarm messenger determines a placeholder for the image tag and indicates to the central server the size of the image to follow.

4. A system for monitoring and reporting medical alarms comprising:
    an alarm messenger which receives an alarm signal from monitored equipment, said alarm signal including information indicative of a location of the monitored equipment, said alarm messenger outputting an alarm messenger signal, including the information, said alarm messenger signal including a text tag and an image tag, the alarm messenger signal as first transmitted from the alarm messenger to a central server has an empty attribute for the image tag, the alarm messenger sending the text portion of the alarm message signal with an expected image instruction to the central server as the alarm signal, the central server transmitting the alarm signal to an appropriate staff.

5. The system of claim 4, wherein the alarm messenger determines an appropriate placeholder for the image tag and indicates to the central server the size of the image to follow.

6. A system for monitoring and reporting medical alarms, the system comprising:
    an alarm messenger which receives alarm signals from a plurality of patient monitoring equipment which monitor a plurality of patients for medical alarm situations and generate the alarm signals, each alarm signal being in an equipment specific format and including information identifying a medical alarm situation that triggered the alarm signal, a location of the equipment sending each alarm signal, and an identifier of the equipment sending each alarm signal;
    a central server which:
        receives the alarm signals from the alarm messenger,
        translates the information included in the alarm signals to a generic format,
        determines a location of the monitor equipment which generated each alarm signal,
        determines a response and identifies staff to respond to each alarm signal, and
        transmits response instructions and location information to the identified staff.

7. The system of claim 6, wherein the central server includes a master association table which maps equipment identification information, patient identification information, bed identification information, room identification information and staff identification information.

8. The system of claim 7, wherein said master association table includes rules governing a method in which the identified staff is notified regarding the alarm situation, the rules being a function of two or more of the equipment identification information, the patient identification information, the bed identification information the room identification information, alarm sensitivity and the staff identification information.

9. The system of claim 7, wherein the central server determines a predefined location to which the equipment is assigned; and produces an alarm if the location of the monitored equipment is not the same as the predefined location.

10. The system of claim 6, further comprising an orchestrator, the orchestrator communicating with the central server, the central server sending each alarm signal to the orchestrator, and the orchestrator sending a signal to the central server to authorize processing of the alarm signal as a function of a sensitivity of the alarm signal.

11. The system of claim 10, wherein the decision to authorize the central server to send the alarm signal is manually made.

12. The system of claim 6, further comprising an assignments table storing information regarding assignments of at least one of equipment and staff to at least one of a time period, a bed, and a physical location.

13. The system of claim 12, further comprising an assignment templates table storing an index of each of the assignments stored in the assignment table, the central server modifying the assignments by amending the assignments tables by utilizing the assignment templates table to access the desired assignments table.

14. The system of claim 13, further including:
- an orchestrator, the orchestrator communicating with the central server, the central server sending the alarm information to the orchestrator, and the orchestrator sending a signal to the central server to authorize processing of an alarm signal as a function of a sensitivity of an alarm signal; and
- wherein said orchestrator provides a graphical user interface for an operator to input modifications to assignments to the server for operation thereon by the server.

15. The system of claim 14, wherein the central server activates an assignment in response to a manual input from the orchestrator.

16. The system of claim 12, wherein the central server activates assignments utilizing the assignment template to select the assignment to be activated from the assignments table.

17. The system of claim 16, further comprising a scheduler for causing the central server to activate an assignment in response to a predetermined schedule.

18. The system of claim 6, further comprising a location-based application compatible device assigned to at least one staff member; a database in the central server storing at least one zone corresponding to geographical locations within a monitored facility; the central server monitors the location based compatible device to determine the physical location of the closest at least one staff member to the equipment generating the alarm signal and notifying a closest member of the staff of the alarm condition.

19. The system of claim 6, further comprising a location-based enabled tag affixed to at least one equipment; a database in the central server storing at least one zone within which the equipment is permitted to be located; the central server sending out an alarm if the equipment leaves the permitted zone.

20. The system of claim 6, further comprising a location based application compatible device assigned to at least one equipment; a database of the central server storing one or more zones corresponding to geographical locations within a monitored facility; the central server monitoring the location base compatible device to determine the physical location of the equipment.

21. The system of claim 6, further comprising a location based application compatible device assigned to at least one staff member; a database of the central server storing at least one zone corresponding to a geographical location within the monitored facility and a pre-determined zone in which the at least one staff member is entitled to be present; the central server sending out an alarm if the at least one staff member leaves the permitted zone.

* * * * *